(12) United States Patent
Twomey et al.

(10) Patent No.: US 9,113,882 B2
(45) Date of Patent: Aug. 25, 2015

(54) METHOD OF MANUFACTURING AN ELECTROSURGICAL INSTRUMENT

(75) Inventors: John R. Twomey, Longmont, CO (US); James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 815 days.

(21) Appl. No.: 13/355,829

(22) Filed: Jan. 23, 2012

(65) Prior Publication Data

US 2013/0185922 A1 Jul. 25, 2013

(51) Int. Cl.
*A61B 18/08* (2006.01)
*B29C 45/14* (2006.01)

(52) U.S. Cl.
CPC ............ *A61B 18/085* (2013.01); *B29C 45/14* (2013.01)

(58) Field of Classification Search
CPC ............ A61B 18/085; A61B 18/087; A61B 2018/087; A61B 18/1442; A61B 18/1445; A61B 18/14; A61B 18/1042; A61B 18/12; A61B 17/00; A61B 2017/00526; A61B 2018/1452; A61B 2018/126; A61B 2018/00607; B29C 45/14; B29C 43/18; B29C 2043/181
USPC ........ 29/748, 758, 592.1, 825, 854, 857, 858, 29/887, 861, 874, 876; 264/272.11, 255, 264/279, 274, 259
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| 5,674,220 A | 10/1997 | Fox et al. |
| H1745 H | 8/1998 | Paraschac |
| D402,028 S | 12/1998 | Grimm et al. |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Sarang Afzali (57) ABSTRACT

A method for manufacturing a pair of jaw members configured for use with an electrosurgical forceps is provided. One or more pairs of seal plates are stamped from a sheet metal. The seal plates are positioned into respective mold cavities. An insulative substrate is introduced into the respective mold cavities. The insulative substrate is allowed to harden in the respective mold cavities to form respective jaw housings with seal plates secured thereto. The jaw housings are removed from the respective mold cavities to form a pair of jaw members.

15 Claims, 4 Drawing Sheets

(56) References Cited

U.S. PATENT DOCUMENTS

| | | | |
|---|---|---|---|
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| 6,852,016 B2 | 2/2005 | Henderson | |
| D502,994 S | 3/2005 | Blake, III | |
| 6,908,463 B2 | 6/2005 | Treat et al. | |
| D509,297 S | 9/2005 | Wells | |
| D525,361 S | 7/2006 | Hushka | |
| 7,083,618 B2 | 8/2006 | Couture et al. | |
| D531,311 S | 10/2006 | Guerra et al. | |
| 7,135,020 B2* | 11/2006 | Lawes et al. | 606/51 |
| D533,274 S | 12/2006 | Visconti et al. | |
| D533,942 S | 12/2006 | Kerr et al. | |
| 7,147,638 B2 | 12/2006 | Chapman et al. | |
| D535,027 S | 1/2007 | James et al. | |
| 7,160,299 B2 | 1/2007 | Baily | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| 7,396,265 B2 | 7/2008 | Darley et al. | |
| D575,395 S | 8/2008 | Hushka | |
| D575,401 S | 8/2008 | Hixson et al. | |
| D582,038 S | 12/2008 | Swoyer et al. | |
| 7,668,597 B2 | 2/2010 | Engmark et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,877,853 B2 | 2/2011 | Unger et al. | |
| D649,249 S | 11/2011 | Guerra | |
| D649,643 S | 11/2011 | Allen, IV et al. | |
| 2003/0216733 A1 | 11/2003 | McClurken et al. | |
| 2005/0021026 A1 | 1/2005 | Baily | |
| 2006/0141861 A1 | 6/2006 | Darley et al. | |
| 2009/0082766 A1 | 3/2009 | Unger et al. | |
| 2009/0082769 A1 | 3/2009 | Unger et al. | |
| 2009/0216229 A1* | 8/2009 | Chojin | 606/52 |
| 2010/0178139 A1 | 7/2010 | Sundar et al. | |
| 2010/0179543 A1* | 7/2010 | Johnson et al. | 606/45 |
| 2010/0204697 A1* | 8/2010 | Dumbauld et al. | 606/51 |
| 2011/0073246 A1 | 3/2011 | Brandt et al. | |
| 2011/0082494 A1 | 4/2011 | Kerr et al. | |
| 2011/0162796 A1 | 7/2011 | Guerra | |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| EP | 2 092 905 | 8/2009 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.

(56) References Cited

OTHER PUBLICATIONS

U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011 Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.

(56) References Cited

OTHER PUBLICATIONS

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'L Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report Ep 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.

(56) References Cited

OTHER PUBLICATIONS

Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Extended European Search Report corresponding to EP 13 15 2329.2, dated May 7, 2013 and completed Apr. 25, 2013; (6 pp).

* cited by examiner

METHOD OF MANUFACTURING AN ELECTROSURGICAL INSTRUMENT

BACKGROUND

1. Technical Field

The present disclosure relates to an electrosurgical instrument and, more particularly, to a method of manufacturing jaw members configured for use with an electrosurgical forceps.

2. Description of Related Art

Electrosurgical forceps are well known in the medical arts. For example, an electrosurgical endoscopic forceps is utilized in surgical procedures, e.g., laparoscopic surgical procedures, where access to tissue is accomplished through a cannula or other suitable device positioned in an opening on a patient. The endoscopic forceps, typically, includes a housing, a handle assembly including a movable handle, a drive assembly, a shaft and an end effector assembly attached to a distal end of the shaft. The endoscopic forceps may utilize both mechanical clamping action and electrical energy to effect hemostasis by heating the tissue and blood vessels to coagulate, cauterize, seal, cut, desiccate, and/or fulgurate tissue. In particular, the jaw members operably communicate with the drive assembly to manipulate tissue, e.g., grasp tissue, and the jaw members have respective seal plates secured to the jaw housing of the respective jaw members to seal tissue.

Manufacturing the jaw members of the end effector, typically, is a complex and lengthy process. In particular, the intricate components of the jaw members are, initially, machined and, subsequently, assembled. As can be appreciated, this adds to the overall costs of the manufacture of the endoscopic forceps.

SUMMARY

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides a method for manufacturing a pair of jaw members configured for use with an electrosurgical forceps. One or more pairs of seal plates are stamped from a sheet metal. The seal plates are positioned into respective mold cavities. An insulative substrate is introduced into the respective mold cavities. The insulative substrate is allowed to harden in the respective mold cavities to form respective jaw housings with seal plates secured thereto. And, the jaw housings are removed from the respective mold cavities to form a pair of jaw members.

According to a further aspect of the instant disclosure, the method may include deforming the seal plates with a die to form the seal plates with a generally "U" shaped configuration.

According to another aspect of the present disclosure, the method may further positioning a knife channel mold into at least one of the mold cavities to form a knife channel within the respective jaw housing, the knife channel configured for reciprocation of a knife blade therethrough.

According to yet another aspect of the present disclosure, either a one-shot or two-shot injection molding process may be utilized in the step of introducing the insulative substrate.

According to still yet another aspect of the present disclosure, the method may include introducing an insulative substrate that is made from one of a thermosetting plastic and a thermoplastic.

According to another aspect of the present disclosure, the method may include positioning at least one electrode into at least one of the mold cavities. In this instance, the electrode may be configured to sever electrosurgically treated tissue positioned between the pair of jaw members upon activation thereof.

In certain instances, deforming the seal plates may include deforming the seal plates to include a pinch trim configured to facilitate securing the seal plates to respective insulative jaw housings.

In certain instances, positioning the seal plates may include positioning the seal plates in the mold cavities such that the seal plates extend a predetermined distance past a top surface of the respective insulative jaw housings when the insulative jaw housings have hardened.

The method may include the step of securing the pair of jaw members to a distal end of the electrosurgical forceps.

An aspect of the present disclosure provides a method for manufacturing a pair of jaw members configured for use with an electrosurgical forceps. One or more pairs of seal plates are stamped from a sheet metal. The stamped out seal plates are deformed with a die to provide the seal plates with a sealing surface portion and a structural insert portion. The seal plates are positioned into respective mold cavities. A curable insulative substrate is introduced into the respective mold cavities such that the insulative substrate covers the structural insert portion of the seal plates. The insulative substrate is allowed to cure in the respective mold cavities to form respective jaw housings with seal plates secured thereto. And, the jaw housings are removed from the respective mold cavities to form a pair of jaw members.

According to a further aspect of the instant disclosure, the method may include deforming the seal plates with a die to form the seal plates with a generally "U" shaped configuration.

According to another aspect of the present disclosure, the method may further positioning a knife channel mold into at least one of the mold cavities to form a knife channel within the respective jaw housing, the knife channel configured for reciprocation of a knife blade therethrough.

According to still yet another aspect of the present disclosure, the method may include introducing a curable insulative substrate that is made from one of a thermosetting plastic and a thermoplastic.

According to another aspect of the present disclosure, the method may include positioning at least one electrode into at least one of the mold cavities. In this instance, the electrode may be configured to sever electrosurgically treated tissue positioned between the pair of jaw members upon activation thereof.

In certain instances, deforming the seal plates may include deforming the seal plates to include a pinch trim configured to facilitate securing the seal plates to respective insulative jaw housings.

In certain instances, positioning the seal plates may include positioning the seal plates in the mold cavities such that the seal plates extend a predetermined distance past a top surface of the respective insulative jaw housings when the insulative jaw housings have hardened.

The method may include the step of securing the pair of jaw members to a distal end of the electrosurgical forceps.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
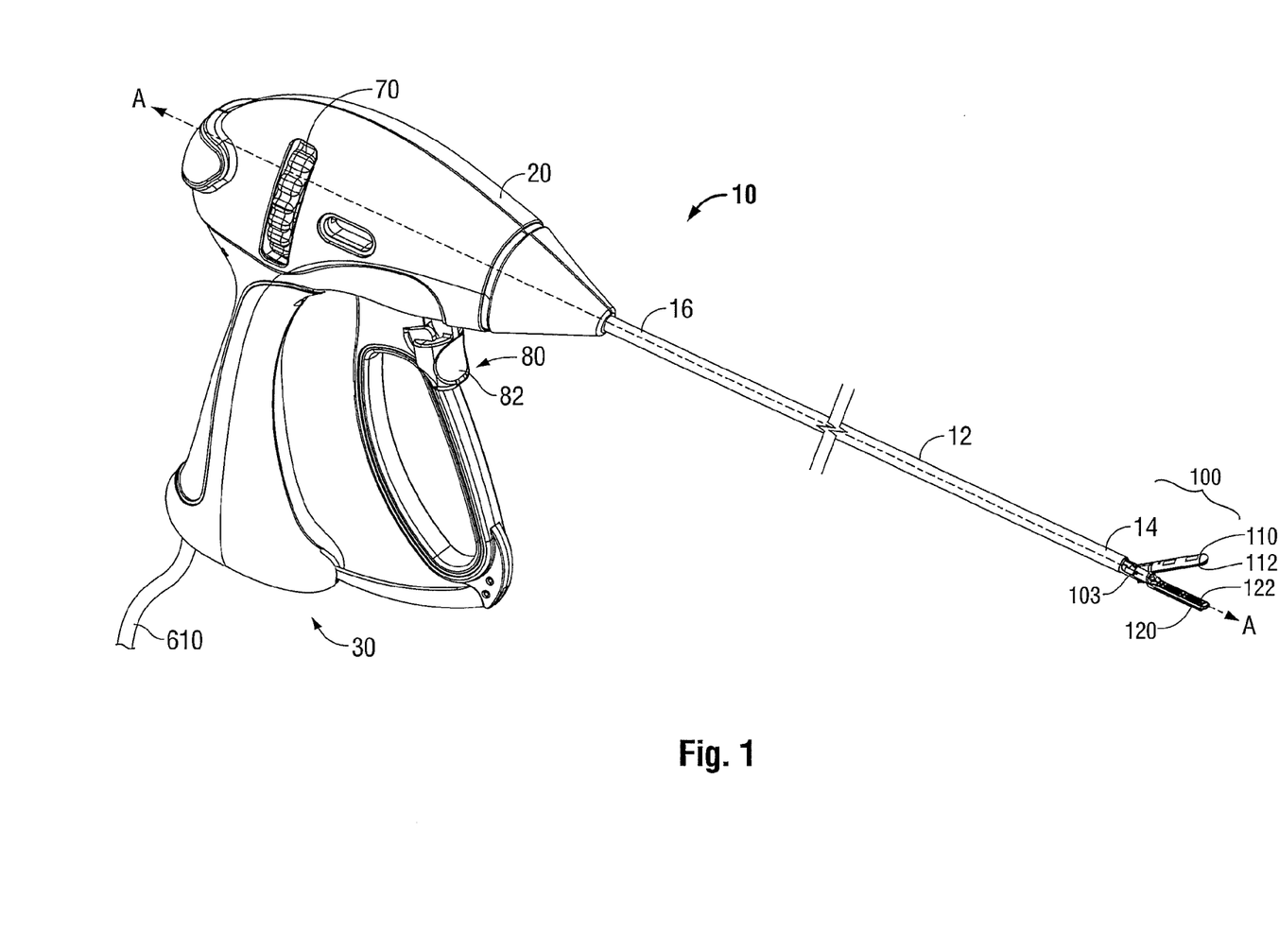
FIG. 1 is a perspective view of an endoscopic electrosurgical forceps utilizing an end effector including jaw members manufactured according to an embodiment of the present disclosure.

Turning now to FIG. 1, an electrosurgical endoscopic forceps 10 (forceps 10) is provided having a longitudinal axis "A-A" defined therethrough, a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not shown) or other suitable power source. Alternately, forceps 10 may be configured as a battery powered instrument. Cable 610 includes one or more wires (not shown) extending therethrough that has sufficient length to extend through shaft 12 in order to provide electrical energy to at least one of the jaw members 110 and 120 of end effector assembly 100.

Continuing with reference to FIG. 1, end effector assembly 100 is designed as a unilateral assembly. In the unilateral jaw assembly jaw member 120 is fixed relative to shaft 12 and jaw member 110 is moveable about a pivot 103 relative to shaft 12 and fixed jaw member 120. End effector assembly 100, however, may alternatively be configured as a bilateral assembly, e.g., where both jaw member 110 and jaw member 120 are moveable about the pivot 103 relative to one another. In some embodiments, a knife assembly is disposed within shaft 12 and a knife channel 13 (FIG. 2B) is defined within one or both jaw members 110, 120 to permit reciprocation of a knife blade 19 therethrough, e.g., via activation of trigger 82 (FIG. 1) of trigger assembly 80. Other than jaw member 110 being movable and jaw member 120 being stationary, jaw members 110 and 120 are identical to one another. In view thereof, and unless otherwise noted, only jaw member 120 is described in detail below.

Figure 2A:
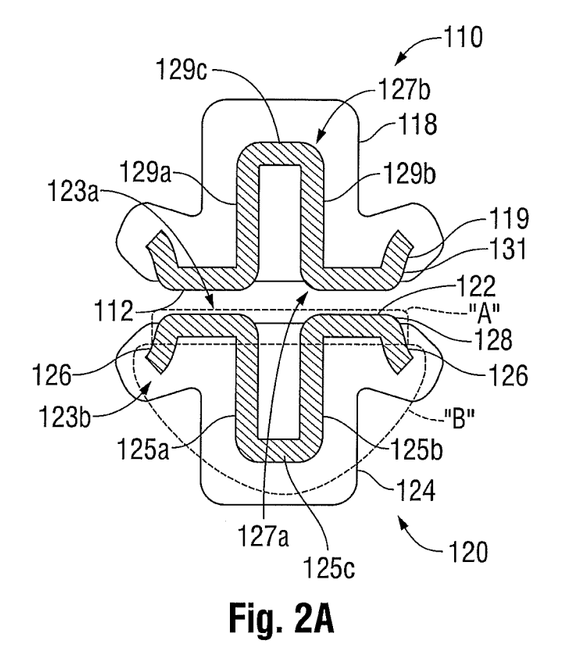
FIG. 2A is a cross-sectional view of the jaw members depicted in FIG. 1.

Turning now to FIG. 2A, jaw members 110 and 120 are illustrated disposed in opposing relation to one another. Jaw member 120 includes a jaw housing 124 that is used to encapsulate a seal plate 122 (FIG. 2A). Jaw housing 124 may be made from any suitable material including, but not limited to, plastic, ceramic material, etc. In the illustrated embodiment, jaw housing 124 is made from plastic and serves as an insulative substrate, described in more detail below. In certain embodiments, it may prove advantageous to provide an exterior portion of the jaw housing 124 that is made from metal and an interior portion (e.g., a portion that is configured to support the seal plate 122 thereon) of the jaw housing 124 that is made from plastic. In this instance, the interior portion serves as an insulative barrier between the seal plate 122 and the exterior portion of the jaw housing 124.

Figure 2B:
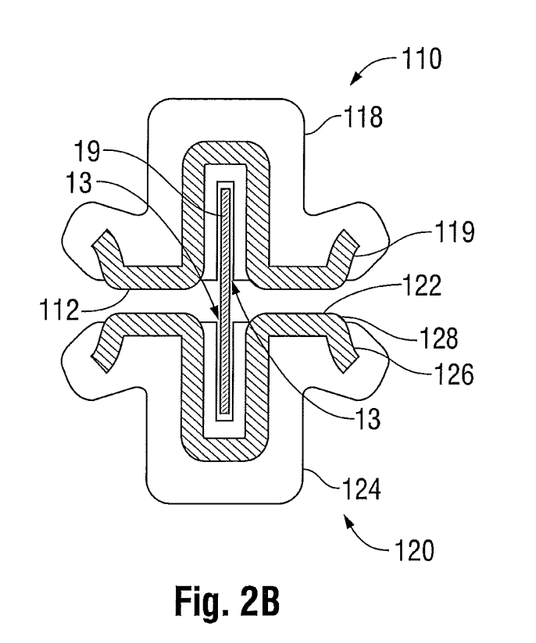
FIG. 2B is a cross-sectional view of jaw members according to another embodiment of the present disclosure.
Figure 2C:
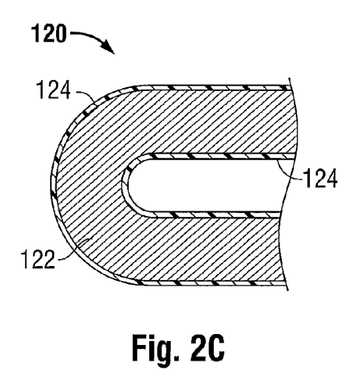
FIG. 2C is a top elevational view of one of the jaw members depicted in FIG. 2B.
Figure 2D:
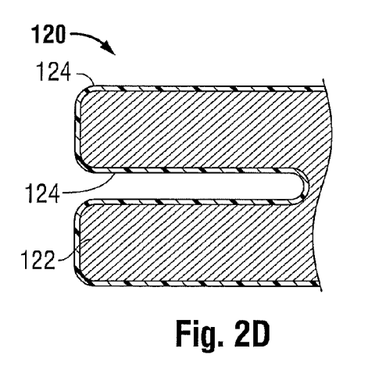
FIG. 2D is a top elevational view of an alternate configuration of the jaw members.
Figure 3:
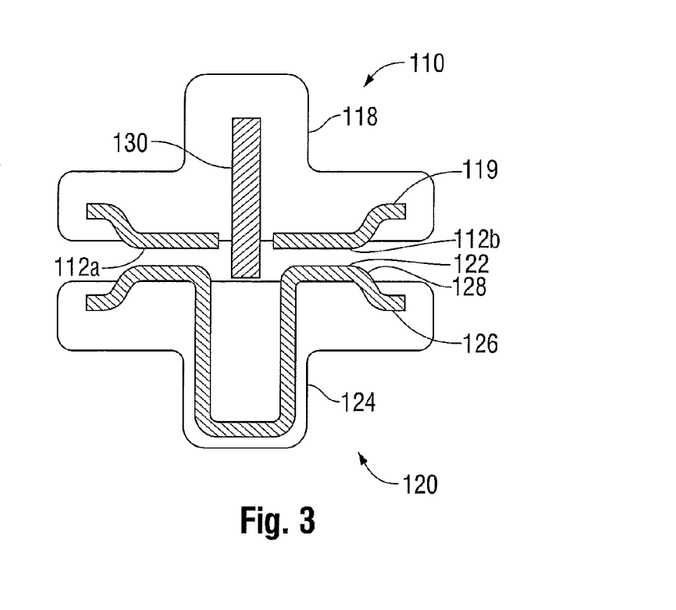
FIG. 3 is a cross-sectional view of an alternate configuration of the jaw members.

Continuing with reference to FIG. 2A, seal plate 122 includes a sealing surface portion 123a (illustrated by phantom lines "A") that is configured to seal tissue and a structural insert portion 123b (illustrated by phantom lines "B") that is configured to secure to jaw housing 124. The structural insert portion 123b of the seal plate 122 includes sidewalls 125a and 125b that extend parallel to one another and converge at back wall 125c. Sealing surface portion 123a has a split configuration having a generally u-shape (as best seen in FIG. 2C). Alternately, the sealing surface portion 123a may have a split configuration having two parallel surfaces that do not meet at a distal end thereof, see FIG. 2C for example. An optional pinch trim 126 may extend along a peripheral edge 128 of the seal surface portion 123a (FIGS. 2A-3). Pinch trim 126 facilitates securing seal plate 122 to the jaw housing 124 during the manufacturing process of the jaw member 120. The seal surface portion 123a and a structural insert portion 123b collectively form a generally "U" configuration (see FIG. 2A, for example), the significance of which described in greater detail below.

Likewise, jaw member 110 includes an opposing electrically conductive tissue sealing plate 112 that includes a sealing surface portion 127a that is configured to seal tissue and a structural insert portion 127b that is configured to secure to jaw housing 118. (FIG. 2A). The structural insert portion 127b includes sidewalls 129a and 129b that extend parallel to one another and converge at a back wall 129c. As with sealing surface portion 123a, sealing surface portion 127a has a split configuration having a generally u-shape and may include a pinch trim 119 that is similar to pinch trim 126. Pinch trim 119 may extend along a peripheral edge 131 of the seal surface portion 127a (FIG. 2A). The seal surface portion 127a and a structural insert portion 127b collectively form a generally "U" cross-section (see FIG. 2A, for example).

Unlike conventional jaw members that are manufactured via a machining process, the jaw members 110 and 120 of the instant disclosure are manufactured via a stamping and overmolding process. Initially, and in one particular embodiment, a pair of seal plates 112 and 122 is formed via a stamping process. Sheet metal of suitable configuration is provided (see FIG. 4 at step 202). In the illustrated embodiments, a stamping or machine press (not shown) is utilized to cut or "punch" the sheet-metal to a desired configuration (see FIG. 4 at step 204). Subsequently, the stamping press is utilized to shape the "punched" sheet-metal into one or more suitable configurations by deforming it with a die or other suitable device (not shown). In accordance with the instant disclosure, the seal plates 112 and 122 are formed with the generally "U" cross-section corresponding to a finished configuration of the respective jaw housings 118 and 124, as best seen in FIGS. 2A and 2B. It has been observed that this "U" cross-section provides the requisite structural rigidity for the respective jaw housing 118 and 124 of the jaw members 110 and 120.

In accordance with the present disclosure, the aforementioned stamping process may include a variety of other sheet-metal manufacturing processes, such as, for example, blanking, embossing, bending, flanging, and coining. In this instance, the stamping process could be a single stage operation where every stroke of the stamping press produces a desired form on a sheet-metal part, or could occur through a series of stages. For example, it may prove advantageous to bend the seal plates 112 and 122 (or portions thereof) after the seal plates 112 and 122 have been deformed by the die. In certain instances, for example, the peripheral edges 128 and 131 may be bent to form the respective pinch trims 126 and 119.

After the sheet-metal is formed into the seal plates 112 and 122, each seal plate 112 and 122 is positioned into a mold cavity (not shown) of suitable configuration (see FIG. 4 at step 206) and overmolded with an insulative substrate (see FIG. 4 at step 206) that substantially encapsulates the seal plates 112 and 122 and forms the outer jaw housing 118 and 124 of the respective jaw members 110 and 120 (FIG. 2A). The mold cavity is shaped to correspond to a desired jaw housing configuration. In one particular embodiment, such as the illustrated embodiment, the mold cavity may be configured to provide jaw members 110 and 120 with a lower jaw profile when compared to conventional jaw members. Advantages of having jaw members 110 and 120 with a lower jaw profile include, but are not limited to better visualization around the jaws, better access to critical structures and contouring of the jaw members 110 and 120 such that the jaw members 110 and 120 can be used for dissection of tissue.

In one particular embodiment, the insulative substrate, such as, for example, a thermoplastic or thermosetting plastic in liquid form, is fed into a barrel (not shown), which may be heated, mixed, and introduced into the mold cavity where it cools and hardens (or cures) to the configuration of the mold cavity. A "single-shot" or "two-shot" injection molding process may be utilized to introduce the liquid insulative substrate into the mold cavity (see FIG. 4 at step 208).

Pinch trims 119 and 126 of the respective seal plates 112 and 122 (FIG. 2A) facilitate securing the seal plates 112 and 122 to the respective insulative jaw housings 118 and 124 during the manufacturing process. That is, the pinch trims 119 and 126 are encapsulated by the liquid insulative substrate during the overmolding process to reinforce the bond between the insulative housing 118 and 124 and the respective sealing surface portions 127a and 123a.

In certain embodiments, such as the embodiment illustrated in FIG. 2B, it may prove advantageous to provide one or more knife channels 13 on one or both of the jaw members 110 and 120. In this instance, the step of overmolding the seal plates 112 and 122 with an insulative substrate includes forming a knife channel 13 in the insulation of each seal plate 112 and 122. In this instance, before the insulating substrate is allowed to harden, a knife channel mold (not shown) is positioned in the mold cavity, e.g., between the sidewalls 129a, 129b and 125a, 125b of seal plates 112 and 122, respectively. In certain instances, this may be accomplished prior to introducing the liquid insulative substrate into the mold cavity.

Figure 4:
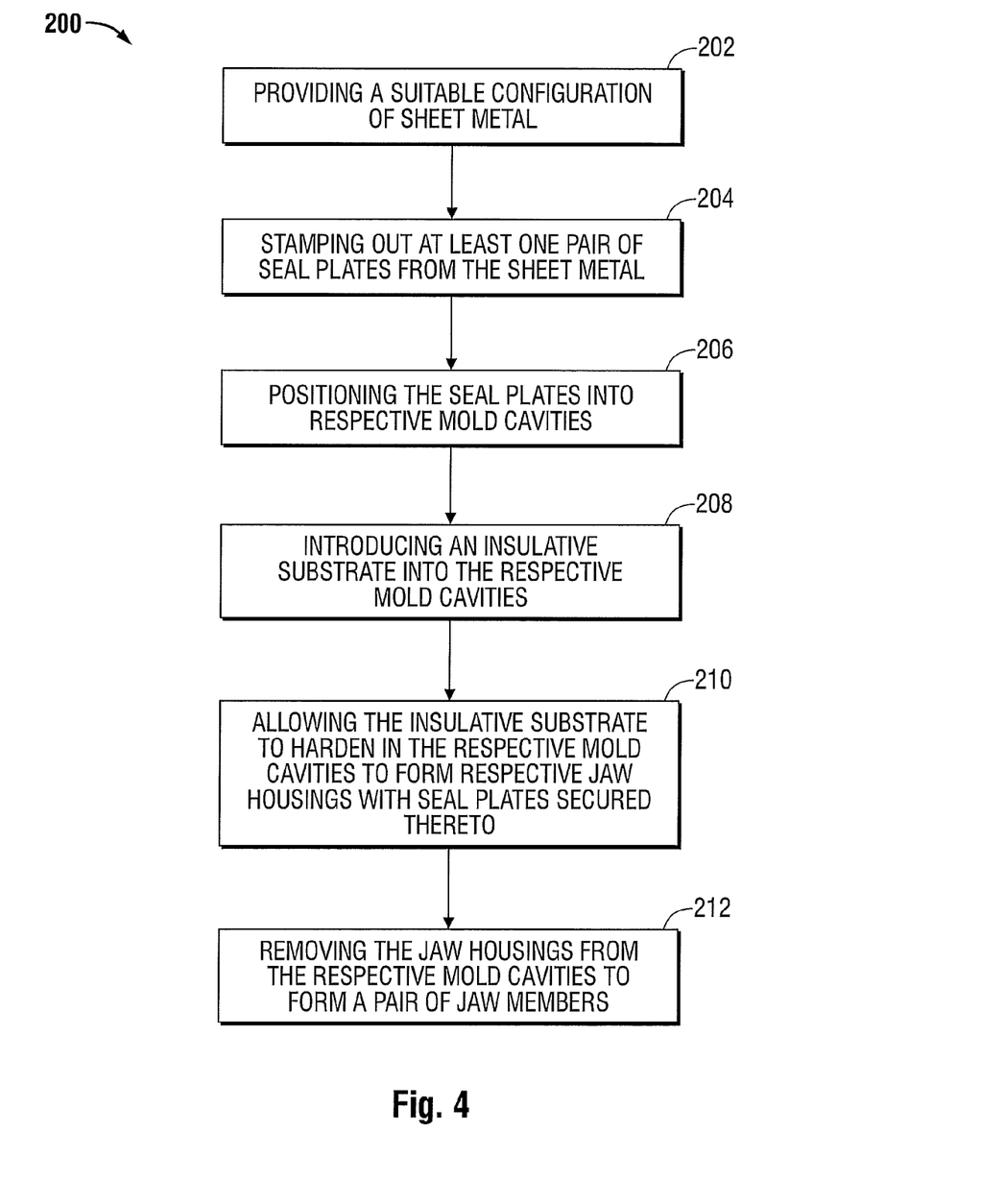
FIG. 4 is a flow-chart illustrating a method of manufacture of the end effector assembly depicted in FIG. 1 according to an embodiment of the present disclosure.

After the insulative substrate hardens and the insulative jaw housings 118 and 124 are formed (see FIG. 4 at step 210), the insulative jaw housing 118 and 124 including the respective seal plates 112 and 122 secured thereto may be removed from their respective mold cavities (see FIG. 4 at step 212). The knife mold may be removed at any time after the insulative substrate hardens. In the hardened (or cured) configuration, the seal plates 112 and 122 extend a predetermined distance past a top surface of the respective insulative jaw housings 118 and 124 (FIG. 2A). In addition, the seal plates 112 and 122 will follow an overall contour of the insulative jaw housings 118 and 124, respectively; this is illustrated in FIG. 2C with respect to seal plate 122 and jaw housing 124.

In an assembled configuration, the jaw members 110 and 120 are secured to the distal end 14 of the shaft via one or more suitable securement methods. As with conventional jaw member configurations, jaw members 110 and 120 are operable to grasp and, subsequently, seal tissue.

The aforementioned stamping and overmolding process utilized to manufacture jaw members 110 and 120 is a simple and low cost alternative to conventional machining processes.

In addition, the aforementioned stamping and overmolding process provides jaw members 110 and 120 with lower profiles when compared to conventional jaw members. As can be appreciated, a forceps 10 that includes jaw members 110 and 120 with low profiles may be better suited in surgical procedures where access to a surgical site is through an access port of relatively small configuration, e.g., less than 5 mm.

Further, while not discussed in great detail above, electrical pathways can be created in the insulative jaw housing 118 and 124 by leaving portions of the seal plates 118 and 128 exposed from the insulative jaw housing 118 and 124 (e.g., at a proximal end of the respective jaw housings 118 and 124) during the overmolding process (alternately, wires may be soldered to the seal plates 118 and 128 prior to the overmolding). In this instance, for example, the pivot pin 103 or cam pin (not shown) may be configured to transmit electrosurgical energy to the seal plates 118 and 124. Accordingly, the need for a wire (or wires) extending through the shaft 12 may be eliminated, which, in turn, may decrease the overall manufacturing cost of the forceps 10.

From the foregoing, and with reference to the various figure drawings, those skilled in the art will appreciate that certain modifications can also be made to the present disclosure without departing from the scope of the same. For example, in certain embodiments, it may prove advantageous to utilize an electrode 130 (FIG. 3) instead of a knife blade to sever tissue. In this instance, one or both of the jaw members, e.g., jaw member 110, may include an electrode 130 in addition to the seal plate 112. In this instance, the step of stamping a pair of seal plates 118 and 128 includes stamping an electrode 130, which may also serve as a structural insert portion for the jaw member 110. In the embodiment illustrated in FIG. 3, jaw member 110 may include a pair of seal plates 112a and 112b (or a seal plate 112 as described above) and the electrode may be positioned therebetween. A method similar to positioning the knife channel mold in the mold cavity may be utilized to position the electrode 130 with respect to the pair of seal plates 112. Unlike the knife channel mold, however, the electrode 130 is configured to remain in the hardened insulative substrate, e.g., the jaw housing 124.

In certain embodiments, the aforementioned mold cavities may be treated with one or more suitable substances configured to facilitate removing the hardened insulative jaw housings 118 and 124 from the mold cavities. Alternately, the mold cavity may be made from one or more non-stick substances, e.g., polytetrafluoroethylene (PTFE).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for manufacturing a jaw member configured for use with an electrosurgical forceps, comprising:
   stamping a seal plate from a sheet metal, wherein the seal plate includes a centrally disposed structural insert portion and two sealing surface portions depending from the structural insert portion, the two sealing surface portions configured to contact tissue and being separated by a gap, wherein an entirety of the seal plate is monolithically formed;
   positioning the seal plate into a mold cavity;
   introducing an insulative substrate into the mold cavity;
   positioning a knife channel mold into the mold cavity such that the knife channel is free from contact with the seal plate, the knife channel configured for reciprocation of a knife blade therethrough;
   allowing the insulative substrate to harden in the mold cavity to form a jaw housing with the seal plate secured thereto; and
   removing the jaw housing from the mold cavity to form the jaw member.

2. The method according to claim 1, including the step of deforming the seal plate with a die to form the seal plate with a generally "U" shaped configuration.

3. The method according to claim 2, wherein the step of deforming the seal plate includes deforming the seal plate to include a pinch trim configured to facilitate securing the seal plate to the jaw housing.

4. The method according to claim 1, wherein one of a one-shot or two-shot injection molding process is utilized in the step of introducing the insulative substrate.

5. The method according to claim 1, wherein the step of introducing the insulative substrate includes introducing an insulative substrate that is made from one of a thermosetting plastic and a thermoplastic.

6. The method according to claim 1, further including the step of positioning at least one electrode into the mold cavity.

7. The method according to claim 1, wherein positioning the seal plate includes positioning the seal plate in the mold cavity such that the seal plate extends a predetermined distance past a top surface of the jaw housing when the jaw housing has hardened.

8. The method according to claim 1, further including the step of securing the jaw member to a distal end of the electrosurgical forceps.

9. A method for manufacturing a jaw member configured for use with an electrosurgical forceps, comprising:
   stamping a seal plate from a single piece of sheet metal;
   deforming the seal plate with a die to provide the seal plate with two sealing surface portions interconnected by a centrally disposed structural insert portion, wherein the two sealing surface portions are separated by a gap;
   positioning the seal plate into a mold cavity;
   introducing a curable insulative substrate into the mold cavity such that the insulative substrate encases the structural insert portion of the seal plate;
   positioning a knife channel mold into the mold cavity such that the knife channel is free from contact with the seal plate, the knife channel configured for reciprocation of a knife blade therethrough;
   allowing the insulative substrate to cure in the mold cavity to form a jaw housing with the seal plate secured thereto; and
   removing the jaw housing from the mold cavity to form a jaw member.

10. The method according to claim 9, wherein the deforming step includes deforming the seal plate such that the sealing surface portions and structural insert portion collectively form the seal plate with a generally "U" shaped configuration.

11. The method according to claim 9, wherein the step of introducing the curable insulative substrate includes introducing a curable insulative substrate that is made from one of a thermosetting plastic and a thermoplastic.

12. The method according to claim 9, further including the step of positioning at least one electrode into the mold cavity.

13. The method according to claim 9, wherein the step of deforming the seal plate includes deforming the seal plate to include a pinch trim configured to facilitate securing the seal plate to the jaw housing.

14. The method according to claim 9, wherein positioning the seal plate includes positioning the seal plate in the mold cavity such that the seal plate extends a predetermined distance past a top surface of the jaw housing when the jaw housing has hardened.

15. The method according to claim 9, further including the step of securing the jaw member to a distal end of the electrosurgical forceps.

* * * * *